US007166686B2

(12) United States Patent
Olson et al.

(10) Patent No.: US 7,166,686 B2
(45) Date of Patent: *Jan. 23, 2007

(54) HIGH REFRACTIVE INDEX PRESSURE-SENSITIVE ADHESIVES

(75) Inventors: David B. Olson, Marine on St. Croix, MN (US); Bettie C. Fong, Woodbury, MN (US); Ying-Yuh Lu, Woodbury, MN (US); Cheryl L. Moore, Afton, MN (US); Todd R. Williams, Lake Elmo, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/171,533

(22) Filed: Jun. 30, 2005

(65) Prior Publication Data

US 2005/0272949 A1    Dec. 8, 2005

Related U.S. Application Data

(63) Continuation of application No. 10/701,218, filed on Nov. 4, 2003, which is a continuation of application No. 09/605,500, filed on Jun. 28, 2000, now Pat. No. 6,663,978.

(51) Int. Cl.
C08F 220/18 (2006.01)

(52) U.S. Cl. ............... 526/319; 526/326; 526/329.2

(58) Field of Classification Search ........... 526/292.3, 526/296, 292.5, 319, 326, 329.2, 284, 286
See application file for complete search history.

(56) References Cited

U.S. PATENT DOCUMENTS

| | | | |
|---|---|---|---|
| 4,683,169 A | 7/1987 | Curry et al. | |
| 4,737,559 A | 4/1988 | Kellen et al. | |
| 5,028,484 A | 7/1991 | Martin et al. | |
| 5,057,366 A | 10/1991 | Husman et al. | |
| 5,274,044 A | 12/1993 | Jalbert et al. | |
| 5,403,901 A | 4/1995 | Namdaran et al. | |
| 5,489,642 A | 2/1996 | Gleichenhagen et al. | |
| 5,626,996 A | 5/1997 | Kato et al. | |
| 5,674,960 A | 10/1997 | Namdaran et al. | |
| 5,686,703 A | 11/1997 | Yamaguchi | |
| 5,708,110 A | 1/1998 | Bennett et al. | |
| 5,932,626 A * | 8/1999 | Fong et al. | 522/182 |
| 6,107,364 A * | 8/2000 | Fong et al. | 522/182 |
| 6,261,700 B1 * | 7/2001 | Olson et al. | 428/522 |
| 6,355,754 B1 * | 3/2002 | Olson et al. | 526/296 |
| 6,376,704 B1 | 4/2002 | Olson | |
| 6,416,838 B1 | 7/2002 | Arney et al. | |
| 6,541,591 B2 * | 4/2003 | Olson et al. | 526/284 |
| 6,663,978 B1 * | 12/2003 | Olson et al. | 428/523 |
| 6,953,623 B2 * | 10/2005 | Olson et al. | 428/412 |

FOREIGN PATENT DOCUMENTS

| | | |
|---|---|---|
| DE | 3 321 501 A1 | 12/1984 |
| DE | 3 321 502 A1 | 12/1984 |
| DE | 43 40 297 | 6/1995 |
| EP | 303 430 | 2/1989 |
| EP | 0 126 397 | 9/1989 |
| EP | 0 989 174 A1 | 3/2000 |
| EP | 0989174 | 3/2000 |
| JP | 58-196277 | 11/1983 |
| JP | 59-111114 | 6/1984 |
| JP | SHO 59-189178 | 10/1984 |
| JP | 60-197711 | 10/1985 |
| JP | 2-248482 | 10/1989 |
| JP | 1-278518 | 11/1989 |
| JP | HEI 3-31309 | 2/1991 |
| JP | HEI 3-127771 | 5/1991 |
| JP | HEI 3-220172 * | 9/1991 |
| JP | 3-296584 | 12/1991 |
| JP | HEI 6-70209 | 9/1994 |
| JP | HEI 7-3237 | 1/1995 |
| JP | 7-331207 | 12/1995 |
| JP | 8-503506 | 4/1996 |
| JP | 9-194798 | 7/1997 |
| JP | HEI 11-5952 | 1/1999 |
| WO | WO 96/16134 | 5/1996 |
| WO | WO 97/01610 | 1/1997 |

OTHER PUBLICATIONS

Syromyatnikov et al. Aryl(meth)acrylates and polymers based on them, Russian Chemical Reviews 68 (9) 781-799 (1999), published Sep. 1999.

Polymer Handbook, Ed. Brandrup, Immergut, 3rd edition 1989, John Wiley & Sons, published in 1989, pp. 451 to 461, pp. III/1 to III/11 and pp. VI/451 to 461.

Habenicht: "Kleben. Grundlagen, Technologie, Anwendugen", 3rd edition 1997, edited by Springer Verlag, Heidelberg, published 1997, pp. 141 to 149; 178 to 180; 184 to 185 and 220-225.

Product catalogue tesa Industrie-Klebebander, Beiersdorf AG, Hamburg, edition Feb. 1993, excerpt.

Product catalogue teas Industrie-Klebebander, Beiersdorf AG, Hamburg, edition Mar. 1995, excerpt.

Certificate of Experiment (1), Jun. 30, 2005 to Jul. 14, 2005 (marked D3).

(Continued)

Primary Examiner—Robert D. Harlan
(74) Attorney, Agent, or Firm—Carolyn A. Fischer

(57) ABSTRACT

The present invention provides pressure-sensitive adhesives having a refractive index of at least 1.48. The pressure-sensitive adhesives comprise at least one monomer containing a substituted or an unsubstituted aromatic moiety.

3 Claims, No Drawings

OTHER PUBLICATIONS

Certificate of Experiment (2), Jul. 14, 2005 to Jul. 20, 2005 (marked D4).

Handbook of Pressure Sensitive Adhesive Technology, Ed. Donatas Satas, 2nd edition 1989 Van Nostrand Reinhold, New York, published 1989, chapter 15, pp. 396-443 and Appendix 15A, pp. 444 to 456.

Bortnowska-Barela B.: "Synthesis of Copolymers of Tert-Butyl Methacrylate and Halogenated Phenyl Methacrylates for the Production of Optical Adhesives with a High Refractive Index", Rapra Abstract, vol. 31, No. 3, Mar. 1994, p. 118.

* cited by examiner

HIGH REFRACTIVE INDEX PRESSURE-SENSITIVE ADHESIVES

CROSS REFERENCE TO RELATED APPLICATIONS

This application is a continuation of U.S. application Ser. No. 10/701,218, filed Nov. 4, 2003, which is a continuation of U.S. application Ser. No. 09/605,500, filed Jun. 28, 2000, now issued as U.S. Pat. No. 6,663,978.

FIELD OF INVENTION

This invention relates to pressure-sensitive adhesives. More particularly, this invention relates to pressure-sensitive adhesives having a high refractive index.

BACKGROUND OF THE INVENTION

Pressure-sensitive adhesives ("PSAs") are defined herein as adhesives which exhibit permanent tack at room temperature. This property allows pressure-sensitive adhesives to adhere tenaciously upon application with only light finger pressure. PSAs have a balance of properties: adhesion, cohesion, stretchiness, and elasticity. Adhesion refers both to immediate adhesion to a surface and to the bond strength which develops upon application of pressure (often measured as "peel strength"). Cohesion refers to the "shear strength" or resistance of the applied PSA to failure when subjected to shearing forces. Stretchiness refers to the ability to elongate under low stresses. Elasticity refers to a property wherein the material exhibits a retractive force when stretched and retracts when the force is released.

Pressure-sensitive adhesives have many diverse applications including applications in optical products. For certain optical applications, it is useful to match the refractive index (RI) of the adhesive to that of the substrate to which it is applied. This matching of refractive index enhances the optical properties of the construction by reducing glare and reflectance. Glare is defined herein as the average reflectance over a range of 450–650 nanometers and reflectance is defined herein as the process where a fraction of the radiant flux incident on a surface is returned into the same hemisphere whose base is the surface and which contains the incident radiation (see Handbook of Optics, $2^{nd}$ ed., McGraw-Hill, Inc., 1995). Often, the substrate is a polymeric material having refractive indexes in the range of 1.48 to 1.65, for example, polymethyl(meth)acrylate (PMMA) has a RI of 1.489; polycarbonate has a RI of 1.585; and polyethylene terephthalate (PET) has a RI of 1.64.

Known PSAs have RIs of about 1.47 or less. If these PSAs are used in optical applications, glare and reflectance may occur.

Therefore, the need exists for pressure-sensitive adhesives which have high refractive indexes.

SUMMARY OF THE INVENTION

The present invention provides pressure-sensitive adhesives which have a refractive index of at least 1.48. These pressure-sensitive adhesives are particularly suitable for optical applications where the substrate similarly has a high refractive index. The pressure-sensitive adhesives of the present invention advantageously allow for the matching of refractive index which reduces glare and reflectance.

The pressure-sensitive adhesives of the present invention comprise at least one monomer containing a substituted or an unsubstituted aromatic moiety.

One aspect of the present invention is a pressure-sensitive adhesive comprising the reaction product of: (a) at least one monomer selected from the group consisting of a monomeric acrylic or methacrylic acid ester of a non-tertiary alcohol, the alkyl group of which comprises from about 1 to about 12 carbon atoms, preferably from about 4 to about 8 carbons; and (b) at least one monomer containing a substituted or an unsubstituted aromatic moiety.

Another aspect of the present invention is a pressure-sensitive adhesive comprising the reaction product of: (b) at least one monomer containing a substituted or an unsubstituted aromatic moiety; and (c) at least one polar monomer copolymerizable with component (b).

Yet, another aspect of the present invention is a pressure-sensitive adhesive comprising the reaction product of: (a) at least one monomer selected from the group consisting of a monomeric acrylic or methacrylic acid ester of a non-tertiary alcohol, the alkyl group of which comprises from about 1 to about 12 carbon atoms, preferably from about 4 to about 8 carbons; (b) at least one monomer containing a substituted or unsubstituted aromatic moiety; and (c) at least one polar monomer copolymerizable with the monomer(s) of components (a) and (b).

The pressure-sensitive adhesives of the present invention may optionally comprise other monomers, crosslinkers, and additives.

Another embodiment of the present invention is a substrate coated with the pressure-sensitive adhesives of the present invention.

DETAILED DESCRIPTION OF ILLUSTRATIVE EMBODIMENTS

The present invention relates to pressure-sensitive adhesives having a refractive index of at least 1.48. Preferably, the pressure-sensitive adhesives have a refractive index of at least 1.50.

The pressure-sensitive adhesives of the present invention have a high refractive index and yet have a good balance of the four properties relevant for pressure-sensitive adhesives: adhesion, cohesion, stretchiness, and elasticity.

Refractive index is defined herein as the absolute refractive index of a material (e.g., a monomer) which is understood to be the ratio of the speed of electromagnetic radiation in free space to the speed of the radiation in that material, with the radiation being of sodium yellow light at a wavelength of about 583.9 nanometers (nm). The refractive index can be measured using known methods and is generally measured using an Abbe Refractometer.

The pressure-sensitive adhesives of the present invention are acrylate adhesives comprising at least one aromatic monomer which is either substituted or unsubstituted. The pressure-sensitive adhesives may further comprise at least one acrylic monomer selected from the group consisting of a monomeric acrylic or methacrylic acid ester of a non-tertiary alcohol and/or at least one polar monomer. The pressure-sensitive adhesives of the present invention optionally comprise other monomers which may be added to improve the properties of the adhesives, such as crosslinkers, and other additives such as tackifiers or plasticizers.

Acrylic Monomers

The acrylic monomers useful in the pressure-sensitive adhesive of the present invention are typically present at ranges from about 0 to about 93 parts by weight. Useful acrylic monomers include at least one monomer selected from the group consisting of a monomeric acrylic or methacrylic acid ester of a non-tertiary alkyl alcohol, the alkyl group of which comprises from about 1 to about 12 carbon atoms, preferably from about 4 to about 8 carbon atoms, and mixtures thereof.

Suitable acrylic monomers include, but are not limited to, those selected from the group consisting of the esters of acrylic acid or methacrylic acid with non-tertiary alkyl alcohols such as 1-butanol, 1-pentanol, 2-pentanol, 3-pentanol, 2-methyl-1-butanol, 1-methyl-1-butanol, -1-methyl-1-pentanol, 2-methyl-1-pentanol, 3-methyl-1-pentanol, 2-ethyl-1-butanol, 2-ethyl-1-hexanol, 3,5,5-trimethyl-1-hexanol, 3-heptanol, 2-octanol, 1-decanol, 1-dodecanol, and the like, and mixtures thereof. Such monomeric acrylic or methacrylic esters are known in the art and are commercially available.

Aromatic Monomers

The following aromatic monomers are high refractive index acrylic monomers, preferably all of which have homopolymer glass transition temperatures at or below 50° C. These aromatic monomers, when polymerized alone or in the presence of other acrylic monomers, result in PSAs having RIs higher than are otherwise available. By adjusting the ratio of monomers, it is possible to make PSAs having RIs of at least 1.48.

The aromatic monomers of the present invention are represented by the following general Formula (I):

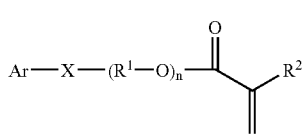

(I)

wherein:
Ar is an aromatic group which is unsubstituted or substituted with a substituent selected from the group consisting of $Br_y$ and $(R^3)_z$
  wherein y represents the number of bromine substituents attached to the aromatic group and is an integer from 0 to 3;
  $R^3$ is a straight or branched alkyl of 2 to 12 carbons; and
  z represents the number of $R^3$ substituents attached to the aromatic ring and is an integer from 0 to 1,
  provided that both y and z are not zero;
X is either oxygen or sulfur;
n is 0 to 3, preferably n is 0 or 1;
$R^1$ is an unsubstituted straight or branched alkyl linking group of 2 to 12 carbons, preferably 2 to 8 carbons; and
$R^2$ is either H or $CH_3$.

In one embodiment of aromatic monomers, X is oxygen. Within this embodiment of aromatic monomers, a group of monomers includes those of Formula (II) wherein Ar is naphthyl:

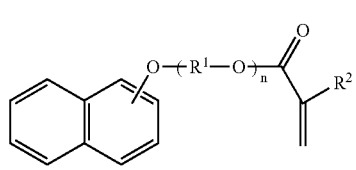

(II)

and $R^1$, $R^2$, and n are as defined above. The naphthyl group is unsubstituted or substituted as described above. Within the group of naphthyl aromatic monomers, another group is that wherein Ar is 1-napthyl or 2-napthyl.

Within the embodiment of aromatic monomers where X is oxygen, another group of monomers includes those of Formula (III) wherein Ar is phenyl:

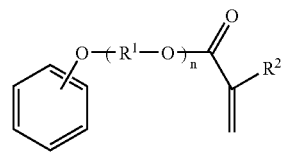

(III)

and $R^1$, $R^2$, and n are as defined above. The phenyl group is unsubstituted or substituted as described above. Within the substituted group of phenyl aromatic monomers, preferably the phenyl is dibromo substituted. Within the bromine substituted group, the phenyl monomers may also be 2-alkyl substituted or 4-alkyl substituted.

In an additional embodiment of aromatic monomers, X is sulfur. Within this embodiment of aromatic monomers, a group of monomers includes those of Formula (IV) wherein Ar is naphthyl:

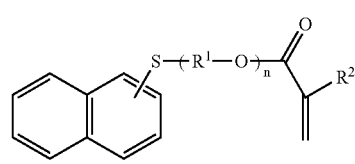

(IV)

and $R^1$, $R^2$, and n are as defined above. The naphthyl group is unsubstituted or substituted as described above. Within the group of naphthyl aromatic monomers, an additional group is that wherein Ar is 1-napthyl or 2-napthyl.

Within the embodiment of aromatic monomers where X is sulfur, another group of monomers includes those of Formula (V) wherein Ar is phenyl:

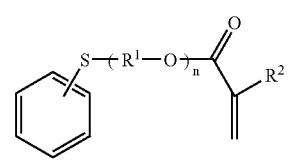

(V)

and $R^1$, $R^2$, and n are as defined above. The phenyl group is unsubstituted or substituted as described above. Within this group of phenyl aromatic monomers, preferably the phenyl is dibromo substituted. In another group, the phenyl monomers may be 2-alkyl substituted or 4-alkyl substituted.

Specific examples of aromatic monomers suitable in the present invention include, but are not limited to, 6-(4,6-dibromo-2-isopropyl phenoxy)-1-hexyl acrylate, 6-(4,6-dibromo-2-sec -butyl phenoxy)-1-hexyl acrylate, 2,6-dibromo-4-nonylphenyl acrylate, 2,6-dibromo -4 -dodecyl phenyl acrylate, 2-(1-naphthyloxy)-1-ethyl acrylate, 2-(2-naphthyloxy)-1-ethyl acrylate, 6-(1-naphthyloxy)-1-hexyl acrylate, 6-(2-naphthyloxy)-1-hexyl acrylate, 8-(1-naphthyloxy)-1-octyl acrylate, 8-(2-naphthyloxy)-1-octyl acrylate, 2-phenylthio-1-ethyl acrylate, and phenoxy ethyl acrylate.

Polar Monomers

Polar monomers can be used to increase the cohesive strength of the pressure-sensitive adhesive. Generally, polar monomers are typically present at ranges from about 0 to about 12 parts by weight, preferably from about 2 to about 8 parts by weight. Useful polar monomers include, but are not limited to, those selected from the group consisting of ethylenically unsaturated carboxylic acids, ethylenically unsaturated sulfonic acids, and ethylenically unsaturated phosphoric acids, and mixtures thereof. Examples of such compounds include, but are not limited to, those selected from the group consisting of acrylic acid, methacrylic acid, itaconic acid, fumaric acid, crotonic acid, citraconic acid, maleic acid, B-carboxyethyl acrylate, sulfoethyl methacrylate, and the like, and mixtures thereof.

Other useful copolymerizable polar monomers include, but are not limited to, acrylamides, N,N-dialkyl substituted acrylamides, N-vinyl lactams, and N,N-dialkylaminoalkyl acrylates, and mixtures thereof. Illustrative examples include, but are not limited to, those selected from the group consisting of N,N-dimethyl acrylamide, N,N-dimethyl methacrylamide, N,N-diethyl acrylamide, N,N-diethyl methacrylamide, N,N-dimethylaminoethyl methacrylate, N,N-dimethylaminopropyl methacrylate, N,N-dimethylaminoethyl acrylate, N,N-dimethylaminopropyl acrylate, and the like, and mixtures thereof.

Preferred polar monomers include acrylic acid, methacrylic acid, itaconic acid, acrylamide, methacrylamide, acrylonitrile, methacrylonitrile, and mixtures thereof.

Crosslinkers

In order to increase the shear or cohesive strength of the PSAs, a crosslinking additive may be incorporated into the PSA.

Two main types of crosslinking additives are commonly used. The first crosslinking additive is a thermal crosslinking additive such as a multifunctional aziridine. One example is 1,1'-(1,3-phenylene dicarbonyl)-bis-(2-methylaziridine) (CAS No. 7652-64-4), referred to herein as "Bisamide". Such chemical crosslinkers can be added into solvent-based PSAs after polymerization and activated by heat during oven drying of the coated adhesive.

In another embodiment, chemical crosslinkers which rely upon free radicals to carry out the crosslinking reaction may be employed. Reagents such as, for example, peroxides serve as a source of free radicals. When heated sufficiently, these precursors will generate free radicals which bring about a crosslinking reaction of the polymer. A common free radical generating reagent is benzoyl peroxide. Free radical generators are required only in small quantities, but generally require higher temperatures to complete a crosslinking reaction than those required for the bisamide reagent.

The second type of chemical crosslinker is a photosensitive crosslinker which is activated by high intensity ultraviolet (UV) light. Two common photosensitive crosslinkers used for hot melt acrylic PSAs are benzophenone and copolymerizable aromatic ketone monomers as described in U.S. Pat. No. 4,737,559. Another photocrosslinker, which can be post-added to the solution polymer and activated by UV light is a triazine, for example, 2,4-bis(trichloromethyl)-6-(4-methoxy-pheynl)-s-triazine. These crosslinkers are activated by UV light generated from artificial sources such as medium pressure mercury lamps or a UV blacklight.

Hydrolyzable, free-radically copolymerizable crosslinkers, such as monoethylenically unsaturated mono-, di-, and trialkoxy silane compounds including, but not limited to, methacryloxypropyltrimethoxysilane (available from Gelest, Inc., Tullytown, Pa.), vinyldimethylethoxysilane, vinylmethyldiethoxysilane, vinyltriethoxysilane, vinyltrimethoxysilane, vinyltriphenoxysilane, and the like, are also useful crosslinking agents.

Multi-functional acrylates are useful for bulk or emulsion polymerization. Examples of useful multi-functional acrylate crosslinking agents include, but are not limited to, diacrylates, triacrylates, and tetraacrylates, such as 1,6-hexanediol diacrylate, poly(ethylene glycol) diacrylates, polybutadiene diacrylate, polyurethane diacrylates, and propoxylated glycerin triacrylate, and mixtures thereof.

Crosslinker is typically present from 0 to about 1 part by weight based on 100 parts by weight adhesive solids.

Crosslinking may also be achieved using high energy electromagnetic radiation such as gamma or e-beam radiation. In this case, no crosslinker may be required.

Chain Transfer Agent

The present invention may optionally further comprise a chain transfer agent. Examples of useful chain transfer agents include, but are not limited to, those selected from the group consisting of carbon tetrabromide, mercaptans, alcohols, and mixtures thereof.

Other Monomers

Other monomers may be added to improve performance, reduce cost, etc. in quantities which do not render the pressure-sensitive adhesive non-tacky. Examples of such other monomers include vinyl esters, vinyl acetate, 2-hydroxyethyl acrylate, styrene, and the like.

Additives

Following copolymerization, other additives may be blended with the resultant acrylate or methacrylate copolymer. For example, compatible tackifiers and/or plasticizers may be added to aid in optimizing the ultimate tack and peel properties of the PSA. The use of such tack-modifiers is common in the art, as is described in the *Handbook of Pressure-Sensitive Adhesive Technology*, edited by Donatas Satas (1982). Examples of useful tackifiers include, but are not limited to, rosin, rosin derivatives, polyterpene resins, coumarone-indene resins, and the like. Plasticizers which may be added to the adhesive of the invention may be selected from a wide variety of commercially available materials. In each case, the added plasticizer must be compatible with the PSA. Representative plasticizers include polyoxyethylene aryl ether, dialkyl adipate, 2-ethylhexyl diphenyl phosphate, t-butylphenyl diphenyl phosphate, di(2-ethylhexyl) adipate, toluenesulfonamide, dipropylene glycol dibenzoate, polyethylene glycol dibenzoate, polyoxypropylene aryl ether, dibutoxyethoxyethyl formal, and dibutoxyethoxyethyl adipate. When used, tackifiers are preferably added in an amount not to exceed about 150 parts by weight per 100 parts by weight copolymer, and plasticizer may be added in an amount up to about 50 parts by weight per 100 parts by weight copolymer.

Polymerization Methods

Adhesives useful in this invention can be polymerized by conventional free-radical polymerization methods. Suitable methods of polymerization include solution polymerization, suspension polymerization, emulsion polymerization, and bulk polymerization.

Substrates

The PSAs of the present invention may be coated upon a variety of flexible and inflexible backing materials using conventional coating techniques to produce PSA-coated sheet materials. Flexible substrates are defined herein as any material which is conventionally utilized as a tape backing or may be of any other flexible material. Examples include, but are not limited to, paper, plastic films such as polypropylene, polyethylene, polyvinyl chloride, polyester (polyethylene terephthalate), polycarbonate, polymethyl(meth) acrylate (PMMA), cellulose acetate, cellulose triacetate, and ethyl cellulose. Additionally, flexible substrates include, but are not limited to, woven fabric formed of threads of synthetic or natural materials such as cotton, nylon, rayon, glass, or ceramic material, or they may be nonwoven fabric such as air-laid webs or natural or synthetic fibers or blends of these. Examples of inflexible substrates include, but are not limited to, metal, metallized polymeric film, or ceramic sheet material. The PSA-coated sheet materials may take the form of any article conventionally known to be utilized with PSA compositions such as labels, tapes, signs, covers, marking indices, and the like.

Method of Application

The PSAs of the present invention may be coated using a variety of conventional coating techniques such as roll coating, knife coating, or curtain coating. The PSAs may also be coated without modification by extrusion, coextrusion, or hot melt techniques by employing suitable conventional coating devices. Primers may be used, but they are not always necessary. The resultant coatings do not require curing or crosslinking. However, if enhancement of resistance to solvents, etc., is desired, crosslinking may be effected by standard methods well-known in the art, such as radiation curing (electron beam or ultraviolet light) or chemical crosslinking.

EXAMPLES

The present invention will be further described with reference to the following non-limiting examples and test methods. All parts, percentages, and ratios are by weight unless otherwise specified.

TABLE OF COMPONENTS

| Abbreviation | Name | Available From |
| --- | --- | --- |
| BA | n-butyl acrylate | BASF Corporation, Parsippany, NJ |
| AA | acrylic acid | BASF Corporation, Parsippany, NJ |
| PEA | phenoxy ethyl acrylate | Sartomer Co., West Chester, PA |
| IOA | iso-octyl acrylate | CPS Chemical Co., Old Bridge, NJ |
| IRGACURE ™ 651 | 2,2-dimethoxy-1,2-diphenylethan-1-one | Ceiba-Geigy, Hawthorne, NY |
| TPO (Lucirin TPO) | diphenyl (2,4,6-trimethylbenzoyl) phosphine oxide | BASF Corporation, Charlotte, NC |
| EB 9220 | hexafunctional aromatic urethane acrylate | UCB Chemicals Corp., Smyrna, GA |
| | 2-isopropylphenol and 2-sec-butylphenol | Schenectedy International, Schenectedy, NY |
| | bromine | Aldrich Chemical Company Inc, Milwaukee, WI |
| | ethyl acetate | |
| | aqueous sodium hydrosulfite | |
| | aqueous sodium carbonate | |
| | sodium iodide | |
| | 6-chlorohexanol | |
| | t-butyl methyl ether | |
| | HCl | |
| | 6-iodohexanol | |
| | Toluene | |
| | Hydroquinone | |
| | p-toluene sulfonic acid | |
| | 4-nonylphenol | |
| | Phenothiazine | |
| | 1-naphthol | |
| | ethylene carbonate | |
| | Triethylamine | |
| | acryloyl chloride | |
| | para-toluene sulfonic acid | |
| | 4-methoxyphenol or methyl hydoquinone | |
| | 2-(phenylthio)ethanol | |
| NPAL | tris(N-nitroso-N-phenylhydroxyl amine) aluminum salt | ChemFirst Fine Chemicals, Pascagoula, MS |
| VAZO ™ 67 | 2,2'-azobis(2-methylbutanenitrile) | E. I. Du Pont De Nemours and Company, Wilmington, DE |
| | N,N'-bis-1,2-propyleneisophthalamide | Xian Modern Chemistry Research Institute of China, Xi'an, China |

-continued

TABLE OF COMPONENTS

| Abbreviation | Name | Available From |
|---|---|---|
| RHODOCAL DS-10 ™ | Sodium dodecylbenzene sulfonate | Rhone-Poulenc North American Chem., Cranbury, NJ |
| | $K_2S_2O_8$ | J. T. Baker Co., Phillipsburg, NJ |

Test Methods

The test methods used to evaluate the PSA coated flexible sheet materials of the examples are industry standard tests. The standard tests are described in various publications of the American Society for Testing and Materials (ASTM), Philadelphia, Pa., and the Pressure Sensitive Tape Council (PSTC).

Shear Strength (ASTM: D3654-78; PSTC-7)

The shear strength is a measure of the cohesiveness or internal strength of an adhesive. It is based upon the amount of force required to pull an adhesive strip from a standard flat surface in a direction parallel to the surface to which it has been affixed with a definite pressure. It is measured in terms of time (in minutes) required to pull a standard area of adhesive coated sheet material from a stainless steel test panel under stress of a constant, standard load.

The tests were conducted on adhesive-coated strips applied to a stainless steel panel such that a 12.7 mm by 12.7 mm portion of each strip was in firm contact with the panel with one end portion of the tape being free. The panel with coated strip attached was held in a rack such that the panel forms an angle of 178° with the extended tape free end which is then tensioned by application of a force of one kilogram applied as a hanging weight from the free end of the coated strip. The 2° less than 180° is used to negate any peel forces, thus insuring that only the shear forces are measured, in an attempt to more accurately determine the holding power of the tape being tested. The time elapsed for each tape example to separate from the test panel is recorded as the shear strength. Unless otherwise noted, all shear failures reported herein are cohesive failures of the adhesive.

Peel Adhesion (ASTM D3330-78 PSTC-1 (11/75))

Peel adhesion is the force required to remove a coated flexible sheet material from a test panel measured at a specific angle and rate of removal. In the examples, this force is expressed in Newtons per 100 mm (N/100 mm) width of coated sheet. The procedure followed is:

1. A 12.7 mm width of the coated sheet is applied to the horizontal surface of a clean glass test plate with at least 12.7 lineal cm in firm contact. A 2 kg hard rubber roller is used to apply the strip.

2. The free end of the coated strip is doubled back nearly touching itself so the angle of removal will be 180°. The free end is attached to the adhesion tester scale.

3. The glass test plate is clamped in the jaws of a tensile testing machine which is capable of moving the plate away from the scale at a constant rate of 2.3 meters per minute.

4. The scale reading in Newtons is recorded as the tape is peeled from the glass surface. The data is reported as the average of the range of numbers observed during the test.

Measurement of Refractive Index

The refractive index of the pressure-sensitive adhesives and cured films were measured using an Abbe Refractometer, Made by Erma Inc., of Tokyo, Japan and distributed by Fisher Scientific.

Monomer Preparation

1. Synthesis of 6-(4,6-dibromo-2-isopropyl phenoxy)-1-hexyl acrylate (DBiPPHA):

In a 12 liter round bottom flask equipped with a mechanical stirrer, condenser, nitrogen cap, addition funnel and temperature probe, 1400 grams of 2-isopropylphenol was mixed with 4630 grams of deionized water. The mixture was stirred with a mechanical mixer and purged with nitrogen for about 10 minutes. 3417 grams bromine was added to the mixture drop-wise through the addition funnel. The temperature was maintained at about 30° C. or less using an ice bath. Following addition of the bromine, the reaction mixture was stirred for 1 hour at room temperature. Reaction completion was determined by gas chromatography, by monitoring the disappearance of the starting material, 2-isopropylphenol, and of monobrominated species.

Upon completion of the reaction, 4075 grams of ethyl acetate was added. The mixture was stirred for 15 minutes and then allowed to phase split. The bottom (aqueous) layer was removed and 2765 grams of a 13 wt. % aqueous sodium hydrosulfite solution was added. The mixture was stirred well and then allowed to phase split. The bottom (aqueous) layer was removed and 2842 grams of a 15 wt. % aqueous sodium carbonate solution was added. The mixture was stirred well and then allowed to phase split. The bottom (aqueous) layer was removed and solvent was stripped from the top layer using a rotary evaporator. This procedure provided approximately 2556 grams of 4,6-dibromo-2-isopropyl phenol (DBiPP).

A 12 liter, four neck, round bottom flask was set up with a mechanical stirrer, condenser, temperature probe and addition funnel in a cooling bath. 800 grams of 4,6-dibromo-2-isopropyl phenol (DBiPP) was added to the flask along with 4902 grams of deionized water and 408 grams of sodium iodide. Using the addition funnel, 435 grams of a 50% sodium hydroxide solution was added while maintaining the temperature below 25° C. The cooling bath was then removed and the reaction mixture was heated to reflux (100° C.). Using a clean addition funnel, 744 grams of 6-chlorohexanol was added over 1 hour and 30 minutes. The reaction was mixed 2 more hours at which point gas chromatography (GC) analysis indicated 0.3% of the starting DBiPP remained unreacted. The solution was cooled and left at room temperature (22–25° C.) overnight.

4196 grams of ethyl acetate was added to the reaction flask and mixed for 10 minutes (t-butyl methyl ether or other suitable organic solvent may be used). The mixture was allowed to phase split. The bottom aqueous layer was removed by vacuum and the pH was recorded at 11. The washing step was repeated a second time using a solution of 27 grams of 37% HCl in 980 grams of deionized water. The aqueous phase that was removed had a pH of 1. The washing step was repeated a third time using 980 grams of a 3% (w/w) aqueous sodium carbonate solution. Again, the aqueous phase was removed and the pH was recorded at 11. The final washing was done with a 4.7% (w/w) aqueous solution of sodium chloride (982 grams). The aqueous phase was again removed by vacuum. The organic phase filtered and concentrated on a rotary evaporator using a water aspirator. Residual solvent was removed using a vacuum pump while stirring the concentrate with a magnetic stirrer. 1250 grams of a yellow liquid was obtained. The yellow liquid was purified by continuous distillation using a rolled film evaporator. First, 6-chlorohexanol and 6-iodohexanol were removed at the following conditions: 130° C. oil bath and 5–20 microns Hg vacuum. The residue was then continuously distilled on the rolled film evaporator using the following conditions: 130° C. oil bath and 1 micron Hg vacuum. 832 grams of the water white alkylated product {6-(4,6-dibromo-2-isopropyl phenoxy)-1-hexanol} was recovered. It can be noted here that optionally, a wiped film evaporator can be used in place of the rolled film evaporator.

A 5 liter, four neck round bottom flask was equipped with a mechanical stirrer, Dean Stark trap, condenser, and temperature probe. The flask was charged with 600 grams of 6-(4,6-dibromo-2-isopropyl phenoxy)-1-hexanol; 2805 grams of toluene; ~200 ppm each of methyl hydroquinone and hydroquinone; 15.2 grams p-toluene sulfonic acid and 131 grams acrylic acid. This mixture was heated to reflux with stirring to azeotrope the water. After 6 hours of refluxing, 30 ml of water had been removed and 99.2% of the 6-(4,6-dibromo-2-iso-propyl phenoxy)-1-hexanol had been converted to 6-(4,6-dibromo-2-iso-propyl phenoxy)-1-hexyl acrylate based on GC analysis. The solution was then cooled and allowed to mix overnight.

828 grams of a 0.27% HCl solution was added to the reaction flask and mixed for 5 minutes. The mixture was allowed to phase split and the aqueous bottom phase (pH=1) was removed by vacuum. The washing was repeated by adding 903 grams of an 8.9% (w/w) aqueous solution of sodium carbonate. The aqueous phase was removed after phase separation. A third wash was done using 867 grams of a 5.1% (w/w) aqueous sodium chloride solution. The aqueous phase was again removed by vacuum. The organic phase was filtered and concentrated on a rotary evaporator using a water aspirator. Residual solvent was removed using a vacuum pump while stirring the concentrate with a magnetic stirrer. 650 grams of a hazy, light yellow liquid was obtained. The yellow liquid was then purified by continuous distillation in a rolled film evaporator using the following conditions: 175° C. oil bath and 1 micron Hg vacuum to give the water white product. NMR analysis indicated a 98.8% purity prior to distillation and a purity of>99% in the distilled product, 6-(4,6-dibromo-2-iso-propyl phenoxy)-1-hexyl acrylate (DBiPPHA).

2. Synthesis of 6-(4,6-dibromo-2-sec-butyl phenoxy)-1-hexyl acrylate (DBsBPHA):

The analogous monomer 6-(4,6-dibromo-2-sec-butyl phenoxy)-1-hexyl acrylate (DBsBPHA) was prepared in the same manner starting with a stoichiometric equivalent amount of 2-sec-butyl phenol rather than the 2-isopropylphenol.

3. Synthesis of 2,6-dibromo-4-nonylphenyl acrylate (DBpNPA):

44 grams (0.2 mole) 4-nonylphenol was mixed in a three neck round bottom flask with 180 grams deionized water. The mixture was stirred with a mechanical stirrer. The reaction solution was purged well with nitrogen. To the flask, 66 grams (0.41 mole) bromine was added dropwise, keeping the reaction temperature about 30° C. After completing the addition, the reaction was stirred for ½ hour at room temperature. The reaction progress was monitored using GC. Because the phenol was a mixture of isomers, an additional 11 grams of bromine was added to react all the starting material.

160 grams ethyl acetate was added with stirring and the mixture was allowed to phase split. The bottom (aqueous) layer was removed. The organic layer was washed sequentially with a pre-mix of 3.5 grams sodium hydrosulfite in 23 grams water and a pre-mix of 3.9 grams sodium chloride in 26 grams water. For each washing, the aqueous premix was stirred well with the organic layer, allowed to phase split and then removed. After the final washing, the solvent was stripped on a rotary evaporator to give a yellow oil.

The yellow oil was distilled using a distillation head and short vigeraux column. The product was distilled at 1.0 mm Hg and a head temperature of 165–170° C. The yield is 66 grams (87%) of light yellow liquid. Analysis by GC and NMR verified the material to be 2,6-dibromo-4-nonylphenol.

30.5 grams (0.08 mole) 2,6-dibromo-4-nonylphenol, 64 grams t-butyl methyl ether, 9.8 grams (0.096 mole) triethyl amine, and 0.005 grams phenothiazine were mixed in a three neck round bottom flask equipped with a mechanical stirrer, temperature probe, and addition funnel. 8.4 grams (0.092 mole) acryloyl chloride was added dropwise. An ice water bath was used to keep the reaction temperature below 20° C. GC shows complete reaction conversion.

45.6 grams deionized water was added, the mixture stirred and allowed to phase split. The lower aqueous phase was removed. The organic layer was washed sequentially with a pre-mix of 0.2 grams concentrated HCl in 8.7 grams deionized water; a pre-mix of 1.7 grams sodium carbonate in 9 grams deionized water; and a pre-mix of 0.8 gram NaCl in 9 grams deionized water. The aqueous pre-mixes were mixed with the organic phase, allowed to phase split, and then discarded. The organic solution was then dried with magnesium sulfate, filtered, and the solvent removed using a rotary evaporator. This method produced 32 grams (92%) of a light yellow oil which was characterized by NMR and GC analysis.

4. Synthesis of 2,6-dibromo-4-dodecylphenyl acrylate (DBpDDPA):

The reactions were run as outlined above, except a stoichiometric equivalent of 4-dodecylphenol was used instead of 4-nonylphenol.

5. Synthesis of 2-(1-naphthyloxy)-1-ethyl acrylate (1-NOEA):

A 5 liter, three neck round bottom flask was equipped with a temperature probe, mechanical stirrer, and condenser. 400 grams 1-naphthol, 269 grams ethylene carbonate and 281 grams triethylamine were added to the flask. Using medium agitation, the batch was heated to 95° C. and began to give off $CO_2$. The batch was held at this temperature for 12 hours, a sample was taken and residual 1-naphthol was determined by GC. Heating of the batch continued at 95° C. until there was less than 3% residual 1-naphthol.

The reaction was then cooled to room temperature and 1470 grams tert-butyl methyl ether and 56 grams triethylamine were added. 0.15 gram hydroquinone and 0.15 gram hydroquinone monomethyl ether were added as inhibitors. To the well-stirred reaction, 289 grams acryloyl chloride was added over a 2–4 hour period, keeping the batch temperature between 25–30° C. The batch was stirred with medium agitation at room temperature for 1 hour after completing the addition. A sample was taken and GC run to determine reaction completion (<1% residual 2-(1-naphthyloxy)-1-ethanol).

The batch was then cooled to room temperature and then washed, first with 400 grams deionized water and 11 grams HCl, then with 250 grams of 15% sodium carbonate in water solution, and then with 250 grams of 20% sodium chloride solution. Residual solvent was removed using a rotary evaporator. The product was a dark colored, low viscosity (<80 cps) liquid (570 grams).

The crude monomer was purified using a continuous a high vacuum rolled film evaporator (available from UIC Inc. of Joliet, Ill.) with the following conditions: 110° C. jacket temperature, 30° C. condenser temperature, 40° C. feed temperature, 300 rpm rotor speed, and 1 micron vacuum. The distillation gave an 80–85% product split. The product, 1-NOEA (475 grams), was a light yellow to orange liquid and was characterized by $^{13}$C NMR and confirmed to be >95% pure.

6. Synthesis of 6-(1-naphthyloxy)-1-hexyl acrylate (1-NOHA):

A 1 liter, three neck flask was equipped with a mechanical stirrer, temperature probe, and a condenser. The following reagents were added: 50 grams 1-naphthol, 312 grams deionized water, 5.2 grams sodium iodide, and 55.4 grams sodium hydroxide (50% solution in water). The mixture was heated to reflux. To the refluxing reaction, 94.7 grams 6-chloro-1-hexanol was added dropwise through an addition funnel over a 2-hour period. Heating at reflux was continued for an additional hour after completing the addition. GC analysis showed <1% residual starting material.

The reaction was cooled to room temperature. 366 grams t-butyl methyl ether was added. The reaction mixture was stirred, then poured into a separatory funnel, and allowed to phase split. The aqueous phase was removed and the organic phase washed with 6.9 grams concentrated HCl in 125 grams deionized water, then with 6.1 grams NaCl in 125 grams deionized water. The remaining solvent was stripped from the product using a rotary evaporator.

The product was distilled at a pot temperature of 220–260° C., head temperature of 200–230° C., at 0.1–0.2 mm Hg. This procedure yielded 63.5 grams of a light brown, somewhat viscous liquid. GC showed it was >98% pure 6-(1-naphthyloxy)-1-hexanol. This material was used in the next step of the synthesis.

A 1 liter, three neck flask, equipped with a mechanical stirrer, temperature probe, and Dean-Stark trap with condenser was charged with the following reagents: 60 grams 6-(1-naphthyloxy)-1-hexanol, 226 grams toluene, 2.5 grams para-toluene sulfonic acid, 21.2 grams acrylic acid, 0.027 gram hydroquinone, and 0.03 gram 4-methoxyphenol. The mixture was heated to reflux, collecting the water which evolved in the Dean-Stark trap. After 3 hours, thin layer chromatography showed the reaction is complete (i.e., no starting material remained).

The reaction was cooled to room temperature and 132 grams of deionized water were added. The mixture was put into a separatory funnel, shaken and allowed to phase split. The aqueous layer was removed and the organic phase was washed with 0.3 gram concentrated HCl in 44 grams deionized water, then with 1.3 grams sodium carbonate in 44 grams deionized water, then with 1.4 grams sodium chloride in 44 grams deionized water. The remaining solvent was stripped using a rotary evaporator. The crude product residue was passed through a flash silica gel column eluting with 5% ethyl acetate/95% heptanes. The product fractions were collected and the solvent stripped using a rotary evaporator. The light greenish oil product crystallized on standing to give 45 grams of off-white crystals with a melting point of 37–39° C. GC and $^{13}$C NMR analysis confirmed the product to be >99% pure 6-(1-naphthyloxy)-1-hexyl acrylate (1-NOHA).

7. Synthesis of 2-phenylthio ethyl acrylate (PTEA):

A 500 ml three neck round bottom flask equipped with a stirrer, vigeraux column and distillation head/receiver was charged with 50 grams (0.32 mole) of 2-(phenylthio) ethanol, 139.5 grams (1.62 mole) methylacrylate, 0.22 gram dibutyltin diacetate, 0.015 gram NPAL and 0.015 gram 4-methoxyphenol. The reaction flask was heated to 100° C. to distill off an azeotrope of methanol and methylacrylate. As the distillation subsided, 150 grams of methylacrylate was added to the flask. This addition procedure was repeated two more times.

Gas chromatographic analysis of the reaction mixture showed <1% unreacted 2-(phenylthio)ethanol. The reaction mixture was then cooled to 50° C. and the residual methylacrylate was removed by vacuum distillation. The product, 2-phenylthio ethyl acrylate (50 grams), was a yellow liquid and was characterized by 13C NMR to be >97% pure.

Preparation of PSAs

The PSAs of the present invention can be made by solution, emulsion or bulk polymerization methods. The procedures for these polymerization methods are described below as Method A, Method B, and Method C, respectively.

Method A—Solution Polymerization

Comparative Example C-1 and Examples 1–14 were prepared using a solution polymerization method. All components were weighed into a glass bottle having a 120 gram capacity. The contents of the bottles were deoxygenated by purging with nitrogen at a flow rate of 1 liter per minute for 35 seconds. The bottles were sealed and placed in a rotating water bath at 57° C. for 24 hours to effect essentially complete polymerization. The polymer solutions were coated onto a 37 micrometer (1.5 mil) polyester film to provide a dry coating thickness of 25 micrometers (~1 mil). The coated film was equilibrated and thereafter tested under conditions of about 23° C. and 50% relative humidity as described by the shear and adhesion test methods. Equilibrated films were utilized to measure refractive index.

Method B—Emulsion Polymerization

Examples 15 and 16 were prepared using an emulsion polymerization method (Method B). All components were added to a 500 ml beaker and mixed until the aqueous and organic phases were homogeneous. The mixture was then homogenized in a Waring Blender for 2 minutes to prepare emulsions for polymerization. The emulsions were placed in glass bottles having a 120 gram capacity. The contents of the bottles were deoxygenated by purging with nitrogen at a flow rate of 1 liter per minute for about 2 minutes. The bottles were sealed and placed in a rotating water bath at 60° C. for 24 hours to effect essentially complete polymerization. After polymerization, the latexes were filtered through cheesecloth to remove coagulum before coating and evaluation. The polymer latexes were coated onto a 37 micrometer (1.5 mil) polyester film to provide a dry coating thickness of about 25 micrometers (~1 mil). The coated films were equilibrated and thereafter tested under conditions of about 23° C. and 50% relative humidity as described by the shear and adhesion test methods. Equilibrated films were utilized to measure refractive index.

Method C—Bulk Polymerization

Examples 17–29 and Comparative Example C-2 were prepared using a bulk polymerization method (Method C). The monomer components were mixed in 250 ml glass bottles to which was added $CBr_4$ (0.2% of total monomer weight) and IRGACURE™ 651 (0.1% of total monomer weight). The contents of the bottles were thoroughly mixed and deoxygenated by purging with nitrogen at a flow rate of 1 liter per minute for 2 minutes. Using a knife coater, the mixtures were coated to a thickness of about 50–80 micrometers (~2–3 mils) between a primed 38 micrometer (1.5 mil) polyester film and a release liner. The resulting coatings were polymerized using ultraviolet radiation under a fluorescent black light (about 680 millijoules/cm$^2$) for about 10 minutes. The coated film was equilibrated and thereafter tested under conditions of about 23° C. and 50% relative humidity as described by the shear and adhesion test methods. Equilibrated films were utilized to measure refractive index as noted above.

Comparative Example C-1

BA/AA 92.5/7.5

16.65 grams butyl acrylate, 1.35 grams acrylic acid, 42 grams acetone, and 0.036 grams VAZO™ 67 free radical initiator were charged into a glass bottle and polymerized as described in Method A. Measured % solids was 28.0%. Refractive index, shear, and adhesion results are given in Table II.

Example 1

BA/AA/1-NOHA 72.5/7.5/20

13.05 grams butyl acrylate, 3.6 grams 1-NOHA, 1.35 grams acrylic acid, 42 grams acetone, and 0.036 grams VAZO™ 67 free radical initiator were charged into a glass bottle and polymerized as described in Method A. Measured % solids were 26.9%. Refractive index, shear, and adhesion results are given in Table II.

Example 2

BA/AA/1-NOHA 52.5/7.5/40

9.45 grams butyl acrylate, 7.2 grams 1-NOHA, 1.35 grams acrylic acid, 42 grams acetone, and 0.036 grams VAZO™ 67 free radical initiator were charged into a glass bottle and polymerized as described according to Method A. Measured % solids was 26.4%. Refractive index, shear, and adhesion results are given in Table II.

Example 3

BA/AA/1-NOEA 72.5/7.5/20

13.05 grams butyl acrylate, 3.6 grams 1-NOEA, 1.35 grams acrylic acid, 42 grams acetone, and 0.036 grams VAZO™ 67 free radical initiator were charged into glass bottle and polymerized as described in Method A. Measured % solids were 28.29%. Refractive index, shear, and adhesion results are given in Table II.

Example 4

BA/AA/1-NOEA 52.5/7.5/40

9.45 grams butyl acrylate, 7.2 grams 1-NOEA, 1.35 grams acrylic acid, 42 grams acetone, and 0.036 grams VAZO™ 67 free radical initiator were charged into a glass bottle and polymerized as described in Method A. Measured % solids was 29.8%. Refractive index, shear, and adhesion results are given in Table II.

Example 5

BA/AA/1-NOEA 85.5/7.5/7

15.39 grams butyl acrylate, 1.26 grams 1-NOEA, 1.35 grams acrylic acid, 42 grams acetone, and 0.036 grams VAZO™ 67 free radical initiator were charged into a glass bottle and polymerized as described in Method A. Measured % solids were 27.5%. Refractive index, shear, and adhesion results are given in Table II.

Example 6

BA/AA/1-NOEA 82.5/7.5/10

14.85 grams butyl acrylate, 1.8 grams 1-NOEA, 1.35 grams acrylic acid, 42 grams acetone, and 0.036 grams VAZO™ 67 free radical initiator were charged into a glass bottle and polymerized as described in Method A. Measured % solids was 27.5%. Refractive index, shear, and adhesion results are given in Table II.

Example 7

BA/AA/1-NOEA 79.5/7.5/13

14.31 grams butyl acrylate, 2.34 grams 1-NOEA, 1.35 grams acrylic acid, 42 grams acetone, and 0.036 grams VAZO™ 67 free radical initiator were charged into a glass bottle and polymerized as described in Method A. Measured % solids were 27.6%. Refractive index, shear, and adhesion results are given in Table II.

Example 8

BA/AA/DBpNPA 72.5/7.5/20

13.05 grams butyl acrylate, 3.6 grams DBpNPA, 1.35 grams acrylic acid, 42 grams acetone, and 0.036 grams VAZO™ 67 free radical initiator were charged into a glass bottle and polymerized as described in Method A. Measured % solids was 29.0%. Refractive index, shear, and adhesion results are given in Table II.

Example 9

BA/AA/DBpNPA 52.5/7.5/40

9.45 grams butyl acrylate, 7.2 grams DBpNPA, 1.35 grams acrylic acid, 42 grams acetone, and 0.036 grams VAZO™ 67 free radical initiator were charged into a glass

Example 10

BA/AA/DBiPPHA 68/2/30

11.42 grams butyl acrylate, 5.04 grams DBiPPHA, 0.34 grams acrylic acid, 42.7 grams ethyl acetate, 0.432 grams isopropyl alcohol, and 0.025 grams VAZO™ 67 free radical initiator were charged into a glass bottle and polymerized as described according to Method A. 0.1% by weight N,N'-bis-1,2-propyleneisophthalamide crosslinker was added to just prior to coating. Refractive index, shear, and adhesion results are given in Table II.

Example 11

BA/AA/DBiPPHA 38/2/60

6.38 grams butyl acrylate, 10.08 grams DBiPPHA, 0.34 grams acrylic acid, 42.3 grams ethyl acetate, 0.864 grams isopropyl alcohol, and 0.025 grams VAZO™ 67 free radical initiator were charged into a glass bottle and polymerized as described according to Method A. 0.1% by weight N,N'-bis-1,2-propyleneisophthalamide crosslinker was added to just prior to coating. Refractive index, shear, and adhesion results are given in Table II.

Example 12

IOA/AA/PTEA 68/2/30

16.32 grams iso-octyl acrylate, 7.2 grams PTEA, 0.48 grams acrylic acid, 36 grams ethyl acetate, and 0.048 grams VAZO™ 67 free radical initiator were charged into a glass bottle and polymerized as described according to Method A. Refractive index, shear, and adhesion results are given in Table II.

Example 13

IOA/AA/PTEA 58/2/40

13.92 grams iso-octyl acrylate, 9.6 grams PTEA, 0.48 grams acrylic acid, 36 grams ethyl acetate, and 0.048 grams VAZO™ 67 free radical initiator were charged into a glass bottle and polymerized as described according to Method A. Refractive index, shear, and adhesion results are given in Table II.

Example 14

IOA/AA/PTEA 48/2/50

11.52 grams iso-octyl acrylate, 12 grams PTEA, 0.48 grams acrylic acid, 36 grams ethyl acetate, and 0.048 grams VAZO™ 67 free radical initiator were charged into a glass bottle and polymerized as described according to Method A. Refractive index, shear, and adhesion results are given in Table II.

bottle and polymerized as described in Method A. Measured % solids was 28.0%. Refractive index, shear, and adhesion results are given in Table II.

Example 15

BA/AA/1-NOEA 75/5/20

37.4 grams deionized water, 0.40 gram RHODOCAL DS-10™, 18.75 grams butyl acrylate, 5.0 grams 1-NOEA, 1.25 grams acrylic acid, and 0.05 gram $K_2S_2O_8$ were mixed, emulsified and polymerized as described in Method B. Refractive index, shear, and adhesion results are given in Table II.

Example 16

BA/AA/1-NOEA 61/6/33

37.4 grams deionized water, 0.40 gram RHODOCAL DS-10™, 13.75 grams butyl acrylate, 7.5 grams 1-NOEA, 1.25 grams acrylic acid, and 0.05 gram $K_2S_2O_8$ were mixed, emulsified and polymerized as described in Method B. Refractive index, shear, and adhesion results are given in Table II.

Examples 17–29 and Comparative Example C-2

Comparative Example C-2 and Examples 17–29 were prepared according to Method C using the monomer components noted in Table I below. A premix syrup of 90 parts IOA and 10 parts AA was prepared for these examples. All values in Table I are parts by weight based on a total of 100 parts monomer. Refractive index, shear, and adhesion results are given in Table II.

TABLE I

| Example | IOA/AA Syrup (90/10) | DBiPPHA | DBsBPHA | PEA |
|---|---|---|---|---|
| C-2 | 100 | | | |
| 17 | 80 | 20 | | |
| 18 | 60 | 40 | | |
| 19 | 40 | 60 | | |
| 20 | 20 | 80 | | |
| 21 | | 100 | | |
| 22 | 80 | | 20 | |
| 23 | 60 | | 40 | |
| 24 | 40 | | 60 | |
| 25 | 20 | | 80 | |
| 26 | | | 100 | |
| 27 | 80 | | | 20 |
| 28 | 60 | | | 40 |
| 29 | 40 | | | 60 |

Example 30

DBsBPHA/EB-9220 99/1

A PSA adhesive composition was prepared by mixing 99 parts DBsBPHA, 1 part EB-9220, a hexa-functional aromatic urethane acrylate, and 1.5 parts of TPO photoinitiator (1.5% of total monomer weight) in an appropriately sized container. The mixture was warmed to 65° C. for 15 minutes and then mixed again. The mixture was coated on a polyester film using a knife coater to a thickness of approximately 25 microns. The coated film construction was passed under a 300 watt/cm UV lamp at a speed of 20 ft/min (6.1 m/min) and then heated in a 100° C. oven for 1 minute. Refractive index, shear, and adhesion results are given in Table II.

Example 31

DBiPPHA/EB-9220 99/I

A PSA adhesive composition was prepared as described in Example 30 with the exception that DBiPPHA was used instead of DBsBPHA. Refractive index, shear, and adhesion results are given in Table II.

TABLE II

| Example Formula | PSA Type | Refractive Index | Shear (min) | Adhesion N/100 mm |
|---|---|---|---|---|
| Comparative Example C-1 BA/AA (92.5/7.5) | Solution | 1.4684 | 4.75 | 71 |
| Example 1 BA/AA/1-NOHA(72.5/7.5/20) | Solution | 1.4913 | 10.80 | 59 |
| Example 2 BA/AA/1-NOHA(52.5/7.5/40) | Solution | 1.5141 | 32.80 | 69 |
| Example 3 BA/AA/1-NOEA (72.5/7.5/20) | Solution | 1.4978 | 57.80 | 74 |
| Example 4 BA/AA/1-NOEA(52.5/7.5/40) | Solution | 1.5236 | 749 | 15 |
| Example 5 BA/AA/1-NOEA (85.5/7.5/7) | Solution | 1.4795 | 38 | 67 |
| Example 6 BA/AA/1-NOEA (82.5/7.5/10) | Solution | 1.4848 | 39 | 70 |
| Example 7 BA/AA/1-NOEA (79.5/7.5/13) | Solution | 1.4902 | 36 | 77 |
| Example 8 BA/AA/DBpNPA (72.5/7.5/20) | Solution | 1.4900 | 125 | 17 |
| Example 9 BA/AA/DBpNPA (52.5/7.5/40) | Solution | 1.5137 | 3842 | 2 |
| Example 10 BA/AA/DBiPPHA (68/2/30) | Solution | 1.4886 | 9.0 | 55 |
| Example 11 BA/AA/DBiPPHA (38/2/60) | Solution | 1.5148 | 5 | 81 |
| Example 12 IOA/AA/PTEA (68/2/30) | Solution | 1.5007 | 5.35 | 67 |
| Example 13 IOA/AA/PTEA (58/2/40) | Solution | 1.5112 | 6.90 | 68 |
| Example 14 IOA/AA/PTEA (48/2/50) | Solution | 1.5256 | 6.80 | 64 |
| Example 15 BA/AA/1-NOEA (75/5/20) | Emulsion | 1.4963 | 70 | 52 |
| Example 16 BA/AA/1-NOEA (61/6/33) | Emulsion | 1.5176 | 230 | 47 |
| Comparative Example C-2 IOA/AA (90/10) | Bulk | 1.4704 | 105 | 69 |
| Example 17 IOA/AA/DBiPPHA (72/8/20) | Bulk | 1.4841 | 40 | 75 |
| Example 18 IOA/AA/DBiPPHA (54/6/40) | Bulk | 1.4965 | 4,000 | 82 |
| Example 19 IOA/AA/DBiPPHA (36/4/60) | Bulk | 1.5134 | 7,600 | 90 |
| Example 20 IOA/AA/DBiPPHA (18/2/80) | Bulk | 1.5309 | 2,500 | 91 |
| Example 21 DBiPPHA (100) | Bulk | 1.5568 | 3,200 | 63 |
| Example 22 IOA/AA/DBsBPHA (72/8/20) | Bulk | 1.4834 | 10,000+ | 62 |
| Example 23 IOA/AA/DBsBPHA (54/6/40) | Bulk | 1.4976 | 10,000+ | 57 |
| Example 24 IOA/AA/DBsBPHA (36/4/60) | Bulk | 1.5132 | 10,000+ | 60 |
| Example 25 IOA/AA/DBsBPHA (18/2/80) | Bulk | 1.5283 | 7,600 | 48 |
| Example 26 DBsBPHA (100) | Bulk | 1.5532 | 10,000+ | 40 |

TABLE II-continued

| Example Formula | PSA Type | Refractive Index | Shear (min) | Adhesion N/100 mm |
|---|---|---|---|---|
| Example 27 IOA/AA/PEA (72/8/20) | Bulk | 1.4856 | 10,000+ | 46 |
| Example 28 IOA/AA/PEA (54/6/40) | Bulk | 1.4976 | 10,000+ | 48 |
| Example 29 IOA/AA/PEA (36/4/60) | Bulk | 1.5154 | 10,000+ | 51 |
| Example 30 DBsBPHA/EB-9220 (99/1) | Bulk | 1.5544 | 914 | 37 |
| Example 31 DBiPPHA/EB-9220 (99/1) | Bulk | 1.5580 | 1079 | 30 |

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims as set forth herein as follows.

What is claimed is:

1. A monomer represented by the following formula

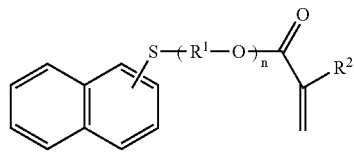

wherein:

$R^1$ is an unsubstituted straight or branched alkyl linking group of 2 to 12 carbons, $R^2$ is either H or $CH_3$, and n is 0 to 3.

2. The monomer according to claim 1, wherein $R^1$ has 2 to 8 carbons.

3. The monomer according to claim 1, wherein n is 0 or 1.